(12) United States Patent
Ezerzer

(10) Patent No.: US 11,078,255 B2
(45) Date of Patent: Aug. 3, 2021

(54) CA2+ REGULATED BINDING AGENTS

(71) Applicant: SYMTHERA CANADA LTD., Ontario (CA)

(72) Inventor: Chai Ezerzer, Ness Ziona (IL)

(73) Assignee: SYMTHERA CANADA LTD., Toronto (CA)

(*) Notice: Subject to any disclaimer, the term of this patent is extended or adjusted under 35 U.S.C. 154(b) by 0 days.

(21) Appl. No.: 16/550,803

(22) Filed: Aug. 26, 2019

(65) Prior Publication Data

US 2020/0062821 A1    Feb. 27, 2020

Related U.S. Application Data

(60) Provisional application No. 62/722,521, filed on Aug. 24, 2018.

(51) Int. Cl.
| | |
|---|---|
| *C07K 14/71* | (2006.01) |
| *C07K 14/47* | (2006.01) |
| *G01N 33/74* | (2006.01) |
| *C07K 14/485* | (2006.01) |

(52) U.S. Cl.
CPC .............. *C07K 14/71* (2013.01); *C07K 14/47* (2013.01); *C07K 14/485* (2013.01); *G01N 33/74* (2013.01); *C07K 2319/00* (2013.01); *G01N 2333/485* (2013.01); *G01N 2333/49* (2013.01)

(58) Field of Classification Search
CPC .. C07K 14/47; C07K 14/4728; C07K 14/485; C07K 14/71; C07K 2319/00; C07K 2319/20; C07K 2319/33; C07K 2319/74; G01N 2333/4727; G01N 2333/485; G01N 2333/49; G01N 33/74
See application file for complete search history.

(56) References Cited

FOREIGN PATENT DOCUMENTS

WO    WO-2016183223 A2 * 11/2016 ........... A61K 49/143

OTHER PUBLICATIONS

Yap et al., Calmodulin Target Database, Journal of Structural and Functional Genomics, vol. 1:8-14 (2000) (Year: 2000).*
Bayley et al., Target recognition by calmodulin: Dissecting the kinetics and affinity of interaction using short peptide sequences, Protein Science, vol. 5:1215-1228 (1996) (Year: 1996).*
Rhoads et al., Sequence motifs for calmodulin recognition, FASEB J., vol. 11:331-340 (1997) (Year: 1997).*
Meister, G.E. et al., "An engineered calmodulin-based allosteric switch for peptide biosensing", ChemBioChem, Aug. 2013 (Aug. 2013), vol. 14, No. 12, pp. 1460-1467.

(Continued)

*Primary Examiner* — Randall L Beane
(74) *Attorney, Agent, or Firm* — Pillsbury Winthrop Shaw Pittman, LLP

(57) ABSTRACT

Disclosed are binding agents that include (a) a calcium binding portion which includes an F-helix peptide and a calcium binding loop peptide derived from an EF-hand motif of a calcium binding protein, wherein the C-terminus of the F-helix peptide is covalently linked to the N-terminus of the calcium binding loop peptide by a peptide bond, and (b) a targeting peptide, wherein the N-terminus of the targeting peptide is covalently linked to the C-terminus of the calcium binding portion by a peptide bond. The binding agents can be used for diagnosis and treatment of various disorders.

7 Claims, 9 Drawing Sheets

Specification includes a Sequence Listing.

(56) References Cited

OTHER PUBLICATIONS

Kobatake, E. et al., "Construction of affinity changeable antibody in response to ca2+", Biotechnology Letters, Jun. 2012 (Jun. 2012), vol. 34, No. 6, pp. 1019-1023.

SantaMaria-Kisiel, L. et al., "Calcium-dependent and -independent interactions of the S100 protein family", Biochemical Journal, Jun. 2006 (Jun. 2006), vol. 396, No. 2, pp. 201-214.

Dreux, A.C. et al., "The epidermal growth factor receptors and their family of ligands: Their putative role in atherogenesis", Atherosclerosis, May 2006 (May 2006), vol. 186, No. 1, pp. 38-53.

Heidaran, M.A. et al., Chimeric a- and β-platelet-derived growth factor (PDGF) receptors define three immunoglobulin-like domains of the a-PDGF receptor that determine PDGF-AA binding specificity, Journal of Biological Chemistry, Nov. 1990 (Nov. 1990), vol. 265, No. 31, pp. 18741-18744.

Rezvanpour, A. et al., "Design of high-affinity S100-target hybrid proteins", Protein Science, Dec. 2009 (Dec. 2009), vol. 18, No. 12, pp. 2528-2536.

International Search Report and Written Opinion of the International Searching Authority dated Dec. 16, 2019 issued in corresponding International Patent Application No. PCT/IB2019/057162.

Mitsuhiko Ikura et al., "Genetic polymorphism and protein conformational plasticity in the calmodulin superfamily: Two ways to promote multifunctionality", PNAS, Jan. 31, 2006, vol. 103, No. 5, pp. 1159-1164.

Kristen M. Vallely et al., "Solution Structure of Human Mts1 (S100A4) as Determined by NMR Spectroscopy", Biochemistry 2002, 41, pp. 12670-12680.

Shibani Bhattacharya et al., "Target selectivity in EF-hand calcium binding proteins", Biochimica et Biophysica Acta 1742 (2004) pp. 69-79.

Gunter Fritz et al., "3D structures of the calcium and zinc binding S100 proteins", Handbook of Metalloproteins, Online 2006, John Wiley & Sons, Ltd., pp. 1-12.

Ingo Marenholz et al., "An update of the S100 nomenclature", Biochimica et Biophysica Acta 1763 (2006) pp. 1282-1283.

Ingo Marenholz et al., "S100 proteins in mouse and man: from evolution to function and pathology (including an update of the nomenclature)", Biochemical and Biophysical Research Communications 322 (2004) pp. 1111-1122.

Graham Carpenter et al., "Epidermal Growth Factor", The Journal of Biological Chemistry, vol. 265, No. 14, Issue of May 15, 1990, pp. 7709-7712.

Joseph Schlessinger et al., "Regulation of Cell Proliferation by Epidermal Growth Factor", CRC Critical Reviews in Biochemistry, vol. 14, Issue 2, pp. 93-111, (1983).

Joachim Krebs et al., "Calcium-binding proteins and the EF hand principle", Calcium: A Matter of Life and Death, 2007, pp. 51-92.

Eugene G. Shpaer, "GeneAssist", Smith-Waterman and Other Database Similarity Searches and Identification of Motifs, Methods in Molecular Biology, vol. 70, Sequence Data Analysis Guidebook, Edited by S R Swindell Human Press Inc., Totowa, NJ, pp. 173-187.

Hongyan Chen et al., "S100 protein family in human cancer", Am. J. Cancer Research, 2014; 4(2), pp. 89-115.

Ravichandran Ramasamy et al., "Advanced glycation end products and RAGE: a common thread in aging, diabetes, neurodegeneration, and inflammation", Glycobiology vol. 15, No. 7, pp. 16R-28R, 2005.

D.B. Zimmer et al., "S100-Mediated Signal Transduction in the Nervous System and Neurolgocial Diseases", Cellular and Molecular Biology, 2005, pp. 201-214.

International Preliminary Report on Patentability dated Dec. 10, 2020, issued in corresponding International Patent Application No. PCT/IB2019/057162 (14 pgs.).

* cited by examiner

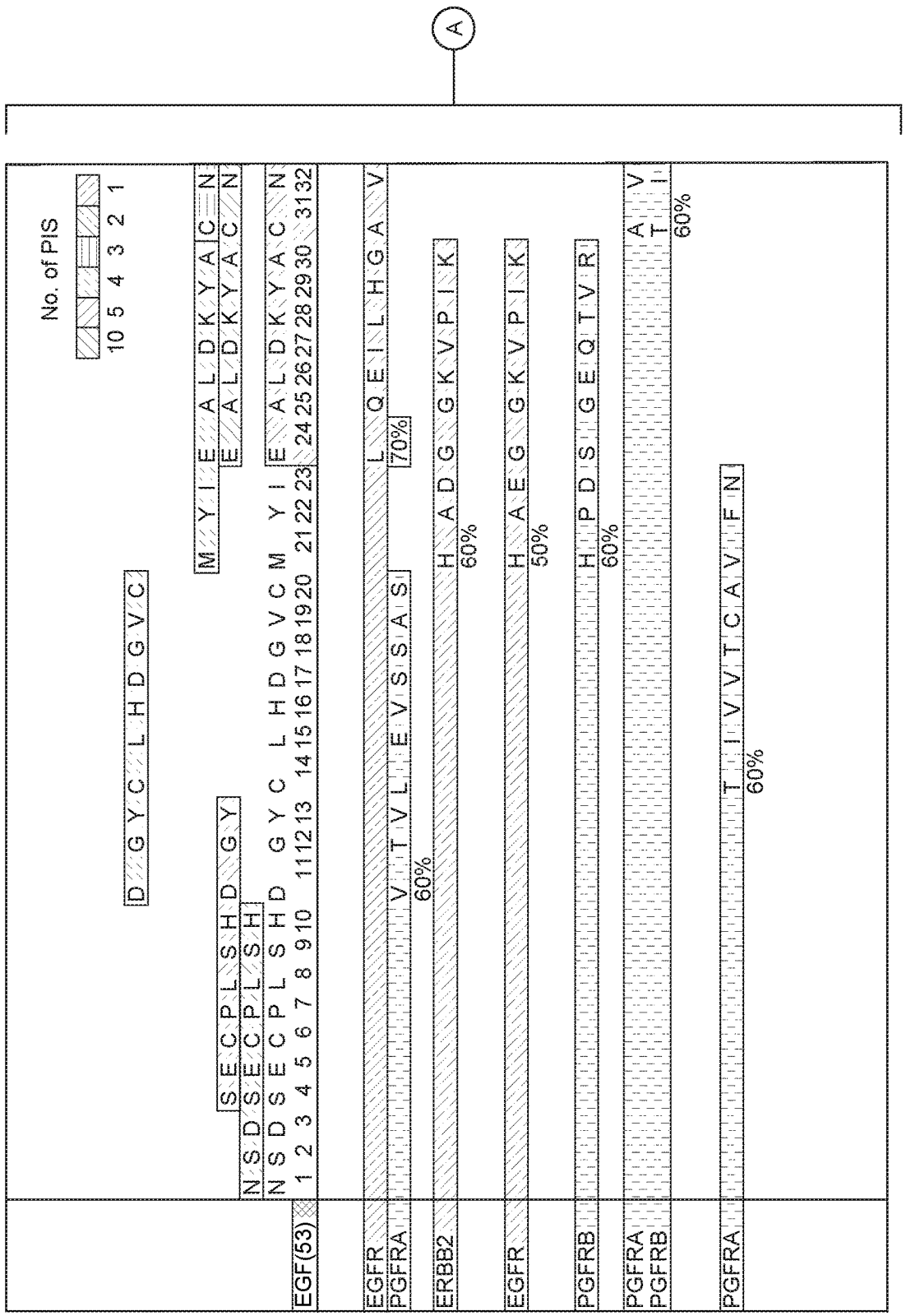
FIG. 1A.1

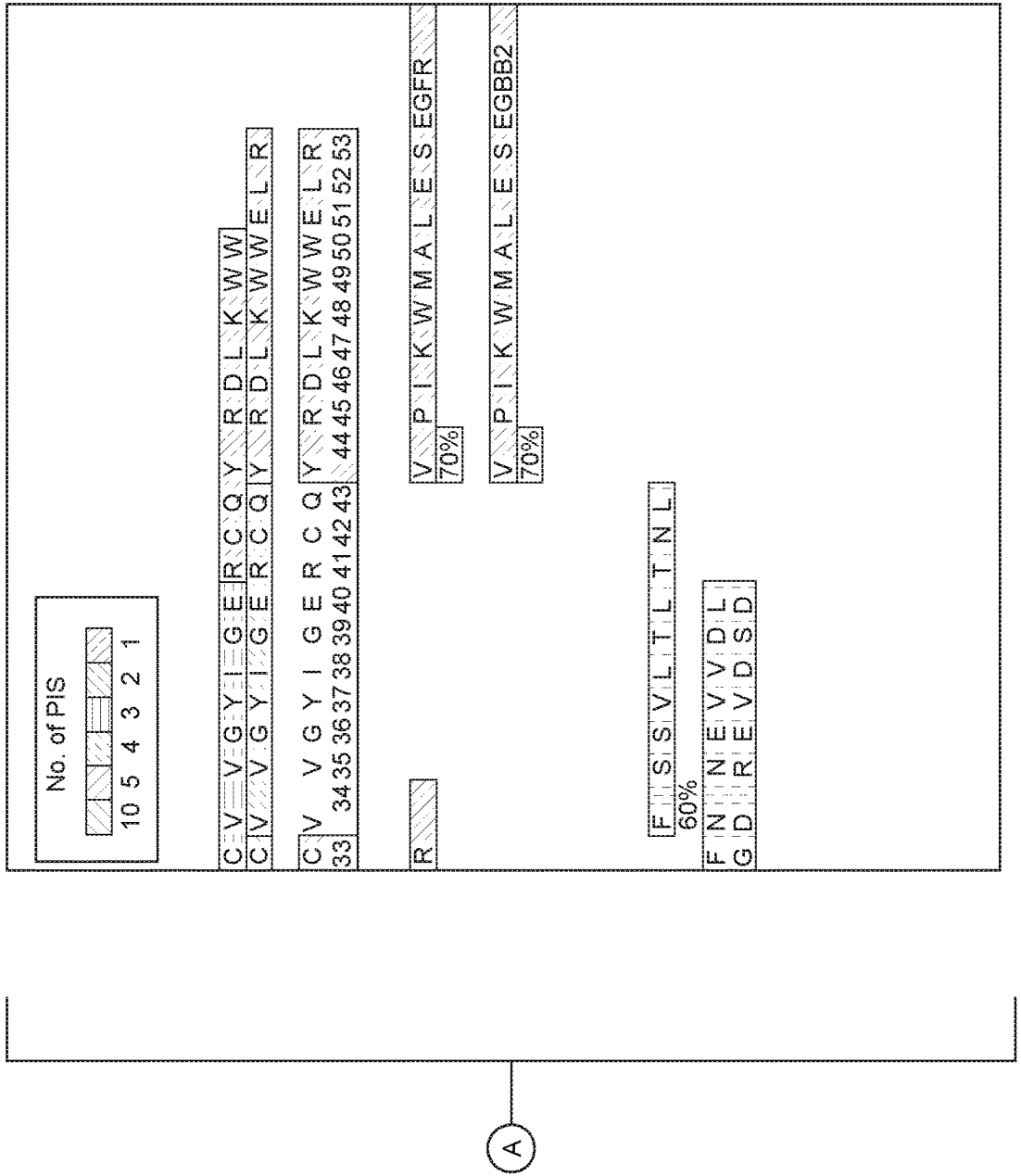
FIG. 1A.2

(A)

| Receptor Name | Peptide | Receptor Site |
|---|---|---|
| EGFR | EALDKYACNC | LQEILHGAVR |
| PGFRA | DGYCLHDGVC | VTVLEVSSAS |
| PGFRB | DGYCLHDGVC | ITIPCRVTDP |
| PGFRP | DGYCLHDGVC | VKVAEAGHYT |
| EGFR | MYIEALDKYA | MRNLQEILHG |
| ERBB2 | MYIEALDKYA | CVNCSQFLRG |
| PGFRB | MYIEALDKYA | HPDSGEQTVR |
| PGFRA | CNCVVGYIGE | AVFNNEVVDL |
| ERBB2 | CNCVVGYIGE | ACAHYKDPPF |
| PGFRA | CNCVVGYIGE | RILHNGAYSL |
| ERBB2 | CNCVVGYIGE | TIGDREVDSD |
| PGFRB | CNCVVGYIGE | IALNTVERIP |
| EGFR | RCQYRDLKWW | NTVERIPLEN |
| EGFR | YRDLKWWELR | YENSYALAVL |
| EGFR | VVGYIGERCQ | HNGAYSLTLQ |
| ERBB2 | VVGYIGERCQ | FSSVLTLTNL |
| PGFRB | VVGYIGERCQ | TIVVTCAVFN |
| PGFRA | CLHDGVCMYI | GLPREYVNAR |
| ERBB2 | SECPLSHDGY | FLTEITEITI |
| PGFRB | SECPLSHDGY | QTVRCTAEGT |
| PGFRA | NSDSECPLSH | VLQGLPREYV |
| ERBB2 | NSDSECPLSH | QTVRCRGRGM |
| PGFRB | NSDSECPLSH | |

| Ligand Name | Peptide | Ligand Site |
|---|---|---|
| EGF | LQEILHGAVRFSSVLTLTNLVPIKWMALES | EALDKYACNCVVGYIGERCQYRDLKWWELR |
| PDGFA | LQEILHGAVRFSSVLTLTNLVPIKWMALES | TSLNPDYREEDTGRPRESGKKRKRKRLKPT |
| PDGFB | LQEILHGAVRFSSVLTLTNLVPIKWMALES | GSQEQRAKTPQTRVTIRTVRRPPKGKHR |

FIG. 1B.1

| CS | NCS | %CS | TS | FOTS | Site Pos | Domain |
|---|---|---|---|---|---|---|
| 12.74 | 10.58 | 0.7 | 2.0146 | 3.11025 | 139 | N-ter |
| 10.89 | 10.92 | 0.6 | 1.7442 | 2.76536 | 181 | N-ter |
| 12.19 | 13.31 | 0.6 | 2.0176 | 3.02576 | 144 | N-ter |
| 15.44 | 4.92 | 0.6 | 1.8392 | 2.96376 | 385 | N-ter |
| 11.51 | 19.07 | 0.6 | 2.2952 | 3.49944 | 136 | N-ter |
| 10.77 | 10.62 | 0.6 | 1.7142 | 2.61182 | 527 | N-ter |
| 14.15 | 13.75 | 0.6 | 2.24 | 3.01874 | 425 | N-ter |
| 12.61 | 7.62 | 0.6 | 1.7182 | 2.32772 | 235 | N-ter |
| 12.44 | 5.94 | 0.6 | 1.6004 | 2.3797 | 585 | N-ter |
| 13.36 | 3.81 | 0.6 | 1.5646 | 2.12828 | 433 | N-ter |
| 9.27 | 3.12 | 0.6 | 1.1142 | 1.77346 | 192 | N-ter |
| 21.61 | 15.99 | 0.6 | 3.1204 | 4.5514 | 90 | N-ter |
| 22.93 | 16.04 | 0.6 | 3.2554 | 5.28328 | 93 | N-ter |
| 16.27 | 7.87 | 0.6 | 2.0992 | 2.7956 | 112 | N-ter |
| 15.54 | 3.83 | 0.6 | 1.7838 | 2.7356 | 436 | N-ter |
| 12.98 | 10.28 | 0.6 | 1.9148 | 2.6956 | 80 | N-ter |
| 9.43 | 17.68 | 0.6 | 2.0038 | 2.75392 | 229 | N-ter |
| 10.14 | 14.17 | 0.6 | 1.8642 | 2.64914 | 548 | N-ter |
| 14.18 | 11.81 | 0.6 | 2.1266 | 3.21992 | 137 | N-ter |
| 9.28 | 9.89 | 0.6 | 1.5214 | 2.20828 | 430 | N-ter |
| 13.27 | 9.71 | 0.6 | 1.9096 | 2.67492 | 545 | N-ter |
| 9.27 | 13.76 | 0.6 | 1.7526 | 2.46076 | 431 | N-ter |

| CS | NCS | %CS | TS | FOTS | Site Pos | Domain |
|---|---|---|---|---|---|---|
| 48.17 | 34.88 | 0.666666667 | 2.380777778 | 3.837722222 | 23 | N-ter |
| 27.99 | 54.41 | 0.4 | 1.658466667 | 2.19656 | 181 | N-ter |
| 27.83 | 58.52 | 0.366666667 | 1.642911111 | 2.033995556 | 194 | N-ter |

FIG. 1B.2

| Peptide Pattern | CK Name | CKR Name | Peptide [EGF] | Site |
|---|---|---|---|---|
| CNCVVGYIGE | EGFR | PAL Peptide | CNCVVGYIGE | ALTEDSIDDT |
| CNCVVGYIGE | ERBB2 | PAL Peptide | CNCVVGYIGE | ACAHYKDPPF |
| CNCVVGYIGE | ERBB2 | PAL Peptide | CNCVVGYIGE | RILHNGAYSL |
| EALDKYACNC | EGFR | PAL Peptide | EALDKYACNC | LQEILHGAVR |
| EALDKYACNC | EGFR | PAL Peptide | EALDKYACNC | LPQPPICTID |
| EALDKYACNC | EGFR | PAL Peptide | EALDKYACNC | LESILHRIYT |
| EALDKYACNC | EGFR | PAL Peptide | EALDKYACNC | GGKVPIKWMA |
| EALDKYACNC | ERBB2 | PAL Peptide | EALDKYACNC | DCQSLTRTVC |
| EALDKYACNC | ERBB2 | PAL Peptide | EALDKYACNC | LPQPPICTID |
| EALDKYACNC | ERBB2 | PAL Peptide | EALDKYACNC | LREVRAVTSA |
| EALDKYACNC | ERBB2 | PAL Peptide | EALDKYACNC | LTEILKGGVL |
| EALDKYACNC | ERBB2 | PAL Peptide | EALDKYACNC | LESILRRRFT |
| EALDKYACNC | ERBB2 | PAL Peptide | EALDKYACNC | GGKVPIKWMA |
| MYIEALDKYA | EGFR | PAL Peptide | MYIEALDKYA | MRNLQEILHG |
| MYIEALDKYA | EGFR | PAL Peptide | MYIEALDKYA | HAEGGKVPIK |
| MYIEALDKYA | ERBB2 | PAL Peptide | MYIEALDKYA | HAEGGKVPIK |
| MYIEALDKYA | ERBB2 | PAL Peptide | MYIEALDKYA | CVNCSQFLRG |
| NSDSECPLSH | EGFR | PAL Peptide | NSDSECPLSH | VAIKELREAT |
| NSDSECPLSH | ERBB2 | PAL Peptide | NSDSECPLSH | VAIKVLRENT |
| RCQYRDLKWW | EGFR | PAL Peptide | RCQYRDLKWW | IALNTVERIP |
| SECPLSHDGY | ERBB2 | PAL Peptide | SECPLSHDGY | GLPREYVNAR |
| VVGYIGERCQ | EGFR | PAL Peptide | VVGYIGERCQ | YENSYALAVL |
| VVGYIGERCQ | EGFR | PAL Peptide | VVGYIGERCQ | DDVDADEYL |
| VVGYIGERCQ | EGFR | PAL Peptide | VVGYIGERCQ | RYSSDPTGAL |
| VVGYIGERCQ | ERBB2 | PAL Peptide | VVGYIGERCQ | HNGAYSLTLQ |
| YRDLKWWELR | EGFR | PAL Peptide | YRDLKWWELR | VPIKWMALES |
| YRDLKWWELR | EGFR | PAL Peptide | YRDLKWWELR | NTVERIPLEN |
| YRDLKWWELR | EGFR | PAL Peptide | YRDLKWWELR | DPQELDILKT |
| YRDLKWWELR | ERBB2 | PAL Peptide | YRDLKWWELR | VPIKWMALES |
| YRDLKWWELR | ERBB2 | PAL Peptide | YRDLKWWELR | QPEQLQVFET |

FIG. 1C.1

| CS | NCS | %CS | TS | FOTS | Site Pos | Domain |
|---|---|---|---|---|---|---|
| 10.8 | 8.33 | 0.6 | 1.5798 | 2.33166 | 1075 | Cytoplasmic |
| 12.44 | 5.94 | 0.6 | 1.6004 | 2.3797 | 585 | N-ter |
| 13.36 | 3.81 | 0.6 | 1.5646 | 2.12828 | 433 | N-ter |
| 12.74 | 10.58 | 0.7 | 2.0146 | 3.11025 | 139 | N-ter |
| 16.27 | 6.67 | 0.6 | 2.0272 | 2.97848 | 932 | Cytoplasmic |
| 11.5 | 14.59 | 0.5 | 1.8795 | 2.5429 | 882 | Cytoplasmic |
| 10.38 | 9.43 | 0.5 | 1.5095 | 2.05055 | 872 | Cytoplasmic |
| 12.36 | 13.81 | 0.6 | 2.0646 | 3.02368 | 210 | N-ter |
| 16.27 | 6.67 | 0.6 | 2.0272 | 2.97848 | 940 | Cytoplasmic |
| 12.56 | 9.1 | 0.6 | 1.802 | 2.7586 | 349 | N-ter |
| 11.28 | 9.15 | 0.6 | 1.677 | 2.53488 | 144 | N-ter |
| 11.5 | 14.32 | 0.5 | 1.866 | 2.519 | 890 | Cytoplasmic |
| 10.38 | 9.43 | 0.5 | 1.5095 | 2.05055 | 880 | Cytoplasmic |
| 11.51 | 19.07 | 0.6 | 2.2952 | 3.49944 | 136 | N-ter |
| 13.57 | 10.66 | 0.5 | 1.89 | 2.49655 | 869 | Cytoplasmic |
| 15.87 | 7.46 | 0.6 | 2.0346 | 2.72942 | 877 | Cytoplasmic |
| 10.77 | 10.62 | 0.6 | 1.7142 | 2.61182 | 527 | N-ter |
| 11.55 | 10.03 | 0.6 | 1.7568 | 2.75156 | 741 | Cytoplasmic |
| 11.16 | 13.37 | 0.5 | 1.7845 | 2.6595 | 749 | Cytoplasmic |
| 21.61 | 15.99 | 0.6 | 3.1204 | 4.5514 | 90 | N-ter |
| 10.14 | 14.17 | 0.6 | 1.8642 | 2.64914 | 548 | N-ter |
| 16.27 | 7.87 | 0.6 | 2.0992 | 2.7956 | 112 | N-ter |
| 11.8 | 7.89 | 0.6 | 1.6534 | 2.42158 | 1007 | Cytoplasmic |
| 9.13 | 10.95 | 0.6 | 1.57 | 2.11782 | 1067 | Cytoplasmic |
| 15.54 | 3.83 | 0.6 | 1.7838 | 2.7356 | 436 | N-ter |
| 22.45 | 14.02 | 0.7 | 3.2264 | 5.23842 | 875 | Cytoplasmic |
| 22.93 | 16.04 | 0.6 | 3.2554 | 5.28328 | 93 | N-ter |
| 20.3 | 13.88 | 0.6 | 2.8628 | 4.41608 | 387 | N-ter |
| 22.45 | 14.02 | 0.7 | 3.2264 | 5.23842 | 883 | Cytoplasmic |
| 20.36 | 6.42 | 0.6 | 2.4212 | 3.851 | 392 | N-ter |
FIG. 1C.2

SEQUENCE LISTING

<160> NUMBER OF SEQ ID NOS: 96

<210> SEQ ID NO 1
<211> LENGTH: 10
<212> TYPE: PRT
<213> ORGANISM: Homo sapiens

<400> SEQUENCE: 1

Glu Ala Leu Asp Lys Tyr Ala Cys Asn Cys
1               5                   10

<210> SEQ ID NO 2
<211> LENGTH: 10
<212> TYPE: PRT
<213> ORGANISM: Homo sapiens

<400> SEQUENCE: 2

Asp Gly Tyr Cys Leu His Asp Gly Val Cys
1               5                   10

<210> SEQ ID NO 3
<211> LENGTH: 11
<212> TYPE: PRT
<213> ORGANISM: Homo sapiens

<400> SEQUENCE: 3

Met Tyr Ile Glu Leu Ala Leu Asp Lys Tyr Ala
1               5                   10

<210> SEQ ID NO 4
<211> LENGTH: 10
<212> TYPE: PRT
<213> ORGANISM: Homo sapiens

<400> SEQUENCE: 4

Cys Asn Cys Val Val Gly Tyr Ile Gly Glu
1               5                   10

<210> SEQ ID NO 5
<211> LENGTH: 10
<212> TYPE: PRT
<213> ORGANISM: Homo sapiens

<400> SEQUENCE: 5

Arg Cys Gln Tyr Arg Asp Leu Lys Trp Trp
1               5                   10

<210> SEQ ID NO 6
<211> LENGTH: 10
<212> TYPE: PRT
<213> ORGANISM: Homo sapiens

<400> SEQUENCE: 6

Tyr Arg Asp Leu Lys Trp Trp Glu Leu Arg
1               5                   10

<210> SEQ ID NO 7
<211> LENGTH: 10
<212> TYPE: PRT
<213> ORGANISM: Homo sapiens

<400> SEQUENCE: 7

Val Val Gly Tyr Ile Gly Glu Arg Cys Gln
1               5                   10

<210> SEQ ID NO 8
<211> LENGTH: 10
<212> TYPE: PRT
<213> ORGANISM: Homo sapiens

<400> SEQUENCE: 8

Cys Leu His Asp Gly Val Cys Met Tyr Ile
1               5                   10

```
<210> SEQ ID NO 9
<211> LENGTH: 10
<212> TYPE: PRT
<213> ORGANISM: Homo sapiens

<400> SEQUENCE: 9

Ser Glu Cys Pro Leu Ser His Asp Gly Tyr
1               5                   10

<210> SEQ ID NO 10
<211> LENGTH: 10
<212> TYPE: PRT
<213> ORGANISM: Homo sapiens

<400> SEQUENCE: 10

Asn Ser Asp Ser Glu Cys Pro Leu Ser His
1               5                   10

<210> SEQ ID NO 11
<211> LENGTH: 12
<212> TYPE: PRT
<213> ORGANISM: Homo sapiens

<400> SEQUENCE: 11

Asp Lys Asp Gly Asp Gly Thr Ile Thr Thr Lys Glu
1               5                   10

<210> SEQ ID NO 12
<211> LENGTH: 12
<212> TYPE: PRT
<213> ORGANISM: Homo sapiens

<400> SEQUENCE: 12

Asp Lys Asp Gly Asp Gly Cys Ile Thr Thr Arg Glu
1               5                   10

<210> SEQ ID NO 13
<211> LENGTH: 12
<212> TYPE: PRT
<213> ORGANISM: Homo sapiens

<400> SEQUENCE: 13

Asp Ala Asp Gly Gly Gly Asp Ile Ser Val Lys Glu
1               5                   10

<210> SEQ ID NO 14
<211> LENGTH: 12
<212> TYPE: PRT
<213> ORGANISM: Homo sapiens

<400> SEQUENCE: 14

Val Leu Gly Ala Glu Asp Gly Cys Ile Ser Thr Lys
1               5                   10

<210> SEQ ID NO 15
<211> LENGTH: 12
<212> TYPE: PRT
<213> ORGANISM: Homo sapiens

<400> SEQUENCE: 15

Asp Lys Gln Gln Arg Gly Lys Ile Lys Ala Thr Asp
1               5                   10
```

```
<210> SEQ ID NO 16
<211> LENGTH: 12
<212> TYPE: PRT
<213> ORGANISM: Homo sapiens

<400> SEQUENCE: 16

Asp Glu Glu Gly Asn Gly Glu Val Lys Thr Gly Glu
1               5                   10

<210> SEQ ID NO 17
<211> LENGTH: 12
<212> TYPE: PRT
<213> ORGANISM: Homo sapiens

<400> SEQUENCE: 17

Asp Lys Asp Gly Asn Gly Tyr Ile Ser Ala Ala Glu
1               5                   10

<210> SEQ ID NO 18
<211> LENGTH: 12
<212> TYPE: PRT
<213> ORGANISM: Homo sapiens

<400> SEQUENCE: 18

Asp Lys Asp Gly Asn Gly Phe Val Ser Ala Ala Glu
1               5                   10

<210> SEQ ID NO 19
<211> LENGTH: 12
<212> TYPE: PRT
<213> ORGANISM: Homo sapiens

<400> SEQUENCE: 19

Asp Lys Glu Lys Lys Gly Tyr Val Met Ala Ser Asp
1               5                   10

<210> SEQ ID NO 20
<211> LENGTH: 12
<212> TYPE: PRT
<213> ORGANISM: Homo sapiens

<400> SEQUENCE: 20

Asp Arg Asn Ala Asp Gly Tyr Ile Asp Pro Glu Glu
1               5                   10

<210> SEQ ID NO 21
<211> LENGTH: 12
<212> TYPE: PRT
<213> ORGANISM: Homo sapiens

<400> SEQUENCE: 21

Asp Lys Asn Ala Asp Gly Tyr Ile Asp Leu Asp Glu
1               5                   10

<210> SEQ ID NO 22
<211> LENGTH: 12
<212> TYPE: PRT
<213> ORGANISM: Homo sapiens

<400> SEQUENCE: 22

Asp Lys Glu Gly Lys Gly Tyr Ile Asp Trp Asn Thr
1               5                   10

<210> SEQ ID NO 23
<211> LENGTH: 12
```

<212> TYPE: PRT
<213> ORGANISM: Homo sapiens

<400> SEQUENCE: 23

Asp Gln Asp Gly Asp Gly His Ile Thr Val Asp Glu
1               5                   10

<210> SEQ ID NO 24
<211> LENGTH: 12
<212> TYPE: PRT
<213> ORGANISM: Homo sapiens

<400> SEQUENCE: 24

Asp Thr Asp Gly Asn Gly Thr Ile Asn Ala Gln Glu
1               5                   10

<210> SEQ ID NO 25
<211> LENGTH: 12
<212> TYPE: PRT
<213> ORGANISM: Homo sapiens

<400> SEQUENCE: 25

Asp Ser Asp Gly Asp Gly Glu Ile Ser Phe Gln Glu
1               5                   10

<210> SEQ ID NO 26
<211> LENGTH: 12
<212> TYPE: PRT
<213> ORGANISM: Homo sapiens

<400> SEQUENCE: 26

Asp Ala Asp Gly Asn Gly Thr Ile Asp Phe Pro Glu
1               5                   10

<210> SEQ ID NO 27
<211> LENGTH: 12
<212> TYPE: PRT
<213> ORGANISM: Homo sapiens

<400> SEQUENCE: 27

Asp Arg Asp Gly Asn Gly Thr Val Asp Phe Pro Glu
1               5                   10

<210> SEQ ID NO 28
<211> LENGTH: 12
<212> TYPE: PRT
<213> ORGANISM: Homo sapiens

<400> SEQUENCE: 28

Asp Glu Asp Gly Ser Gly Thr Ile Asp Phe Glu Glu
1               5                   10

<210> SEQ ID NO 29
<211> LENGTH: 12
<212> TYPE: PRT
<213> ORGANISM: Homo sapiens

<400> SEQUENCE: 29

Asp Glu Asp Gly Ser Gly Thr Val Asp Phe Asp Glu
1               5                   10

<210> SEQ ID NO 30
<211> LENGTH: 12
<212> TYPE: PRT
<213> ORGANISM: Homo sapiens

```
<400> SEQUENCE: 30

Gly Ile Asp Gly Asn Gly Glu Leu Asp Phe Ser Thr
1               5                   10

<210> SEQ ID NO 31
<211> LENGTH: 12
<212> TYPE: PRT
<213> ORGANISM: Homo sapiens

<400> SEQUENCE: 31

Asp Lys Asn Asn Asp Gly Arg Ile Asp Phe Asp Glu
1               5                   10

<210> SEQ ID NO 32
<211> LENGTH: 12
<212> TYPE: PRT
<213> ORGANISM: Homo sapiens

<400> SEQUENCE: 32

Asp Lys Asn Asn Asp Gly Arg Ile Asp Tyr Asp Glu
1               5                   10

<210> SEQ ID NO 33
<211> LENGTH: 12
<212> TYPE: PRT
<213> ORGANISM: Homo sapiens

<400> SEQUENCE: 33

Asp Arg Asp Asn Lys Gly Phe Phe Asn Cys Asp Gly
1               5                   10

<210> SEQ ID NO 34
<211> LENGTH: 12
<212> TYPE: PRT
<213> ORGANISM: Homo sapiens

<400> SEQUENCE: 34

Asp Ile Asp Gly Asp Gly Gln Val Asn Tyr Glu Glu
1               5                   10

<210> SEQ ID NO 35
<211> LENGTH: 12
<212> TYPE: PRT
<213> ORGANISM: Homo sapiens

<400> SEQUENCE: 35

Asp Thr Asp Gly Asp Gly Gln Val Asn Tyr Glu Glu
1               5                   10

<210> SEQ ID NO 36
<211> LENGTH: 12
<212> TYPE: PRT
<213> ORGANISM: Homo sapiens

<400> SEQUENCE: 36

Asp Val Asp Gln Asp Gly Arg Val Asn Tyr Glu Glu
1               5                   10

<210> SEQ ID NO 37
<211> LENGTH: 12
<212> TYPE: PRT
<213> ORGANISM: Homo sapiens

<400> SEQUENCE: 37
```

Asp Lys Asp Gly Asp Arg Thr Ile Asp Tyr Glu Glu
1               5                   10

<210> SEQ ID NO 38
<211> LENGTH: 12
<212> TYPE: PRT
<213> ORGANISM: Homo sapiens

<400> SEQUENCE: 38

Asp Ile Glu Pro Asn Gly Lys Val Lys Tyr Asp Glu
1               5                   10

<210> SEQ ID NO 39
<211> LENGTH: 12
<212> TYPE: PRT
<213> ORGANISM: Homo sapiens

<400> SEQUENCE: 39

Asp Lys Asp Gly Asp Gly Lys Ile Gly Val Asp Glu
1               5                   10

<210> SEQ ID NO 40
<211> LENGTH: 11
<212> TYPE: PRT
<213> ORGANISM: Homo sapiens

<400> SEQUENCE: 40

Leu Gly Thr Val Met Arg Ser Leu Gly Gln Asn
1               5                   10

<210> SEQ ID NO 41
<211> LENGTH: 11
<212> TYPE: PRT
<213> ORGANISM: Homo sapiens

<400> SEQUENCE: 41

Leu Gly Thr Val Met Arg Met Leu Gly Gln Thr
1               5                   10

<210> SEQ ID NO 42
<211> LENGTH: 12
<212> TYPE: PRT
<213> ORGANISM: Homo sapiens

<400> SEQUENCE: 42

Glu Leu Gly Lys Val Met Arg Met Leu Gly Gln Asn
1               5                   10

<210> SEQ ID NO 43
<211> LENGTH: 11
<212> TYPE: PRT
<213> ORGANISM: Homo sapiens

<400> SEQUENCE: 43

Leu Met Val Ala Met Arg Cys Leu Gly Ala Ser
1               5                   10

<210> SEQ ID NO 44
<211> LENGTH: 11
<212> TYPE: PRT
<213> ORGANISM: Homo sapiens

<400> SEQUENCE: 44

Leu Glu Trp Leu Met Ser Leu Leu Gly Ile Asn

<210> SEQ ID NO 45
<211> LENGTH: 11
<212> TYPE: PRT
<213> ORGANISM: Homo sapiens

<400> SEQUENCE: 45

Leu Arg His Val Met Thr Asn Leu Gly Glu Lys
1               5                   10

<210> SEQ ID NO 46
<211> LENGTH: 11
<212> TYPE: PRT
<213> ORGANISM: Homo sapiens

<400> SEQUENCE: 46

Leu Arg His Val Met Thr Arg Leu Gly Glu Lys
1               5                   10

<210> SEQ ID NO 47
<211> LENGTH: 11
<212> TYPE: PRT
<213> ORGANISM: Homo sapiens

<400> SEQUENCE: 47

Leu Arg Ser Lys Leu Thr Ser Leu Gly Glu Lys
1               5                   10

<210> SEQ ID NO 48
<211> LENGTH: 11
<212> TYPE: PRT
<213> ORGANISM: Homo sapiens

<400> SEQUENCE: 48

Leu Ala Glu Ile Phe Arg Ala Ser Gly Glu His
1               5                   10

<210> SEQ ID NO 49
<211> LENGTH: 11
<212> TYPE: PRT
<213> ORGANISM: Homo sapiens

<400> SEQUENCE: 49

Leu Lys Ile Met Leu Gln Ala Thr Gly Glu Thr
1               5                   10

<210> SEQ ID NO 50
<211> LENGTH: 11
<212> TYPE: PRT
<213> ORGANISM: Homo sapiens

<400> SEQUENCE: 50

Leu Lys Tyr Val Leu Met Asn Ala Gly Glu Pro
1               5                   10

<210> SEQ ID NO 51
<211> LENGTH: 11
<212> TYPE: PRT
<213> ORGANISM: Homo sapiens

<400> SEQUENCE: 51

Leu Arg Arg Ala Met Ala Gly Leu Gly Gln Pro
1               5                   10

<210> SEQ ID NO 52
<211> LENGTH: 11
<212> TYPE: PRT
<213> ORGANISM: Homo sapiens

<400> SEQUENCE: 52

Leu Gly Ala Ala Leu Lys Ala Thr Gly Lys Asn
1               5                   10

<210> SEQ ID NO 53
<211> LENGTH: 9
<212> TYPE: PRT
<213> ORGANISM: Homo sapiens

<400> SEQUENCE: 53

Phe Leu Thr Ala Ala Lys Lys Ala Arg
1               5

<210> SEQ ID NO 54
<211> LENGTH: 11
<212> TYPE: PRT
<213> ORGANISM: Homo sapiens

<400> SEQUENCE: 54

Phe Leu Thr Met Met Ala Arg Lys Met Lys Asp
1               5                   10

<210> SEQ ID NO 55
<211> LENGTH: 11
<212> TYPE: PRT
<213> ORGANISM: Homo sapiens

<400> SEQUENCE: 55

Phe Leu Gly Met Met Ala Arg Lys Met Lys Asp
1               5                   10

<210> SEQ ID NO 56
<211> LENGTH: 11
<212> TYPE: PRT
<213> ORGANISM: Homo sapiens

<400> SEQUENCE: 56

Phe Leu Val Met Met Val Arg Gln Met Lys Glu
1               5                   10

<210> SEQ ID NO 57
<211> LENGTH: 11
<212> TYPE: PRT
<213> ORGANISM: Homo sapiens

<400> SEQUENCE: 57

Phe Leu Val Met Met Val Arg Cys Met Lys Asp
1               5                   10

<210> SEQ ID NO 58
<211> LENGTH: 11
<212> TYPE: PRT
<213> ORGANISM: Homo sapiens

<400> SEQUENCE: 58

Phe Leu Thr Ile Met His Met Gln Ile Lys Gln
1               5                   10

<210> SEQ ID NO 59

```
<211> LENGTH: 9
<212> TYPE: PRT
<213> ORGANISM: Homo sapiens

<400> SEQUENCE: 59

Phe Leu Lys Met Met Glu Gly Val Gln
1               5

<210> SEQ ID NO 60
<211> LENGTH: 9
<212> TYPE: PRT
<213> ORGANISM: Homo sapiens

<400> SEQUENCE: 60

Phe Leu Glu Phe Met Lys Gly Val Glu
1               5

<210> SEQ ID NO 61
<211> LENGTH: 11
<212> TYPE: PRT
<213> ORGANISM: Homo sapiens

<400> SEQUENCE: 61

Phe Leu Ala Leu Met Gly Val Tyr His Glu Lys
1               5                   10

<210> SEQ ID NO 62
<211> LENGTH: 8
<212> TYPE: PRT
<213> ORGANISM: Homo sapiens

<400> SEQUENCE: 62

Phe Val Gln Met Met Thr Ala Lys
1               5

<210> SEQ ID NO 63
<211> LENGTH: 7
<212> TYPE: PRT
<213> ORGANISM: Homo sapiens

<400> SEQUENCE: 63

Phe Val Arg Val Leu Ser Lys
1               5

<210> SEQ ID NO 64
<211> LENGTH: 8
<212> TYPE: PRT
<213> ORGANISM: Homo sapiens

<400> SEQUENCE: 64

Phe Ala Arg Met Leu Ala Gln Glu
1               5

<210> SEQ ID NO 65
<211> LENGTH: 11
<212> TYPE: PRT
<213> ORGANISM: Homo sapiens

<400> SEQUENCE: 65

Phe Val Ala Met Met Thr Gly Glu Ser Phe Lys
1               5                   10

<210> SEQ ID NO 66
<211> LENGTH: 11
<212> TYPE: PRT
```

```
<213> ORGANISM: Homo sapiens

<400> SEQUENCE: 66

Phe Ile His Lys Ile Thr Leu Pro Gly Arg Asp
1               5                   10

<210> SEQ ID NO 67
<211> LENGTH: 8
<212> TYPE: PRT
<213> ORGANISM: Homo sapiens

<400> SEQUENCE: 67

Phe Ser Thr Leu Val Ala Glu Ser
1               5

<210> SEQ ID NO 68
<211> LENGTH: 23
<212> TYPE: PRT
<213> ORGANISM: Homo sapiens

<400> SEQUENCE: 68

Asp Lys Asp Gly Asp Gly Thr Ile Thr Thr Lys Glu Leu Gly Thr Val
1               5                   10                  15

Met Arg Ser Leu Gly Gln Asn
            20

<210> SEQ ID NO 69
<211> LENGTH: 23
<212> TYPE: PRT
<213> ORGANISM: Homo sapiens

<400> SEQUENCE: 69

Asp Lys Asp Gly Asp Gly Cys Ile Thr Thr Arg Glu Leu Gly Thr Val
1               5                   10                  15

Met Arg Ser Leu Gly Gln Asn
            20

<210> SEQ ID NO 70
<211> LENGTH: 23
<212> TYPE: PRT
<213> ORGANISM: Homo sapiens

<400> SEQUENCE: 70

Asp Ala Asp Gly Gly Gly Asp Ile Ser Val Lys Glu Leu Gly Thr Val
1               5                   10                  15

Met Arg Met Leu Gly Gln Thr
            20

<210> SEQ ID NO 71
<211> LENGTH: 24
<212> TYPE: PRT
<213> ORGANISM: Homo sapiens

<400> SEQUENCE: 71

Val Leu Gly Ala Glu Asp Gly Cys Ile Ser Thr Lys Glu Leu Gly Lys
1               5                   10                  15

Val Met Arg Met Leu Gly Gln Asn
            20

<210> SEQ ID NO 72
<211> LENGTH: 23
<212> TYPE: PRT
<213> ORGANISM: Homo sapiens
```

<400> SEQUENCE: 72

Asp Lys Gln Gln Arg Gly Lys Ile Lys Ala Thr Asp Leu Met Val Ala
1               5                   10                  15

Met Arg Cys Leu Gly Ala Ser
            20

<210> SEQ ID NO 73
<211> LENGTH: 23
<212> TYPE: PRT
<213> ORGANISM: Homo sapiens

<400> SEQUENCE: 73

Asp Glu Glu Gly Asn Gly Glu Val Lys Thr Gly Glu Leu Glu Trp Leu
1               5                   10                  15

Met Ser Leu Leu Gly Ile Asn
            20

<210> SEQ ID NO 74
<211> LENGTH: 23
<212> TYPE: PRT
<213> ORGANISM: Homo sapiens

<400> SEQUENCE: 74

Asp Lys Asp Gly Asn Gly Tyr Ile Ser Ala Ala Glu Leu Arg His Val
1               5                   10                  15

Met Thr Asn Leu Gly Glu Lys
            20

<210> SEQ ID NO 75
<211> LENGTH: 23
<212> TYPE: PRT
<213> ORGANISM: Homo sapiens

<400> SEQUENCE: 75

Asp Lys Asp Gly Asn Gly Phe Val Ser Ala Ala Glu Leu Arg His Val
1               5                   10                  15

Met Thr Arg Leu Gly Glu Lys
            20

<210> SEQ ID NO 76
<211> LENGTH: 23
<212> TYPE: PRT
<213> ORGANISM: Homo sapiens

<400> SEQUENCE: 76

Asp Lys Glu Lys Lys Gly Tyr Val Met Ala Ser Asp Leu Arg Ser Lys
1               5                   10                  15

Leu Thr Ser Leu Gly Glu Lys
            20

<210> SEQ ID NO 77
<211> LENGTH: 23
<212> TYPE: PRT
<213> ORGANISM: Homo sapiens

<400> SEQUENCE: 77

Asp Arg Asn Ala Asp Gly Tyr Ile Asp Pro Glu Glu Leu Ala Glu Ile
1               5                   10                  15

Phe Arg Ala Ser Gly Glu His
            20

-continued

<210> SEQ ID NO 78
<211> LENGTH: 23
<212> TYPE: PRT
<213> ORGANISM: Homo sapiens

<400> SEQUENCE: 78

Asp Lys Asn Ala Asp Gly Tyr Ile Asp Leu Asp Glu Leu Lys Ile Met
1               5                   10                  15

Leu Gln Ala Thr Gly Glu Thr
            20

<210> SEQ ID NO 79
<211> LENGTH: 23
<212> TYPE: PRT
<213> ORGANISM: Homo sapiens

<400> SEQUENCE: 79

Asp Lys Glu Gly Lys Gly Tyr Ile Asp Trp Asn Thr Leu Lys Tyr Val
1               5                   10                  15

Leu Met Asn Ala Gly Glu Pro
            20

<210> SEQ ID NO 80
<211> LENGTH: 23
<212> TYPE: PRT
<213> ORGANISM: Homo sapiens

<400> SEQUENCE: 80

Asp Gln Asp Gly Asp Gly His Ile Thr Val Asp Glu Leu Arg Arg Ala
1               5                   10                  15

Met Ala Gly Leu Gly Gln Pro
            20

<210> SEQ ID NO 81
<211> LENGTH: 23
<212> TYPE: PRT
<213> ORGANISM: Homo sapiens

<400> SEQUENCE: 81

Asp Thr Asp Gly Asn Gly Thr Ile Asn Ala Gln Glu Leu Gly Ala Ala
1               5                   10                  15

Leu Lys Ala Thr Gly Lys Asn
            20

<210> SEQ ID NO 82
<211> LENGTH: 21
<212> TYPE: PRT
<213> ORGANISM: Homo sapiens

<400> SEQUENCE: 82

Asp Ser Asp Gly Asp Gly Glu Ile Ser Phe Gln Glu Phe Leu Thr Ala
1               5                   10                  15

Ala Lys Lys Ala Arg
            20

<210> SEQ ID NO 83
<211> LENGTH: 23
<212> TYPE: PRT
<213> ORGANISM: Homo sapiens

<400> SEQUENCE: 83

Asp Ala Asp Gly Asn Gly Thr Ile Asp Phe Pro Glu Phe Leu Thr Met

-continued

```
1               5                   10                  15
Met Ala Arg Lys Met Lys Asp
            20

<210> SEQ ID NO 84
<211> LENGTH: 23
<212> TYPE: PRT
<213> ORGANISM: Homo sapiens

<400> SEQUENCE: 84

Asp Arg Asp Gly Asn Gly Thr Val Asp Phe Pro Glu Phe Leu Gly Met
1               5                   10                  15

Met Ala Arg Lys Met Lys Asp
            20

<210> SEQ ID NO 85
<211> LENGTH: 23
<212> TYPE: PRT
<213> ORGANISM: Homo sapiens

<400> SEQUENCE: 85

Asp Glu Asp Gly Ser Gly Thr Ile Asp Phe Glu Glu Phe Leu Val Met
1               5                   10                  15

Met Val Arg Gln Met Lys Glu
            20

<210> SEQ ID NO 86
<211> LENGTH: 23
<212> TYPE: PRT
<213> ORGANISM: Homo sapiens

<400> SEQUENCE: 86

Asp Glu Asp Gly Ser Gly Thr Val Asp Phe Asp Glu Phe Leu Val Met
1               5                   10                  15

Met Val Arg Cys Met Lys Asp
            20

<210> SEQ ID NO 87
<211> LENGTH: 23
<212> TYPE: PRT
<213> ORGANISM: Homo sapiens

<400> SEQUENCE: 87

Gly Ile Asp Gly Asn Gly Glu Leu Asp Phe Ser Thr Phe Leu Thr Ile
1               5                   10                  15

Met His Met Gln Ile Lys Gln
            20

<210> SEQ ID NO 88
<211> LENGTH: 21
<212> TYPE: PRT
<213> ORGANISM: Homo sapiens

<400> SEQUENCE: 88

Asp Lys Asn Asn Asp Gly Arg Ile Asp Phe Asp Glu Phe Leu Lys Met
1               5                   10                  15

Met Glu Gly Val Gln
            20

<210> SEQ ID NO 89
<211> LENGTH: 21
<212> TYPE: PRT
```

```
<213> ORGANISM: Homo sapiens

<400> SEQUENCE: 89

Asp Lys Asn Asn Asp Gly Arg Ile Asp Tyr Asp Glu Phe Leu Glu Phe
1               5                   10                  15

Met Lys Gly Val Glu
            20

<210> SEQ ID NO 90
<211> LENGTH: 23
<212> TYPE: PRT
<213> ORGANISM: Homo sapiens

<400> SEQUENCE: 90

Asp Arg Asp Asn Lys Gly Phe Phe Asn Cys Asp Gly Phe Leu Ala Leu
1               5                   10                  15

Met Gly Val Tyr His Glu Lys
            20

<210> SEQ ID NO 91
<211> LENGTH: 20
<212> TYPE: PRT
<213> ORGANISM: Homo sapiens

<400> SEQUENCE: 91

Asp Ile Asp Gly Asp Gly Gln Val Asn Tyr Glu Glu Phe Val Gln Met
1               5                   10                  15

Met Thr Ala Lys
            20

<210> SEQ ID NO 92
<211> LENGTH: 19
<212> TYPE: PRT
<213> ORGANISM: Homo sapiens

<400> SEQUENCE: 92

Asp Thr Asp Gly Asp Gly Gln Val Asn Tyr Glu Glu Phe Val Arg Val
1               5                   10                  15

Leu Ser Lys

<210> SEQ ID NO 93
<211> LENGTH: 20
<212> TYPE: PRT
<213> ORGANISM: Homo sapiens

<400> SEQUENCE: 93

Asp Val Asp Gln Asp Gly Arg Val Asn Tyr Glu Glu Phe Ala Arg Met
1               5                   10                  15

Leu Ala Gln Glu
            20

<210> SEQ ID NO 94
<211> LENGTH: 23
<212> TYPE: PRT
<213> ORGANISM: Homo sapiens

<400> SEQUENCE: 94

Asp Lys Asp Gly Asp Arg Thr Ile Asp Tyr Glu Glu Phe Val Ala Met
1               5                   10                  15

Met Thr Gly Glu Ser Phe Lys
            20
```

```
<210> SEQ ID NO 95
<211> LENGTH: 23
<212> TYPE: PRT
<213> ORGANISM: Homo sapiens

<400> SEQUENCE: 95

Asp Ile Glu Pro Asn Gly Lys Val Lys Tyr Asp Glu Phe Ile His Lys
1               5                   10                  15

Ile Thr Leu Pro Gly Arg Asp
            20

<210> SEQ ID NO 96
<211> LENGTH: 20
<212> TYPE: PRT
<213> ORGANISM: Homo sapiens

<400> SEQUENCE: 96

Asp Lys Asp Gly Asp Gly Lys Ile Gly Val Asp Glu Phe Ser Thr Leu
1               5                   10                  15

Val Ala Glu Ser
            20
```

CA2+ REGULATED BINDING AGENTS

CROSS-REFERENCE TO RELATED APPLICATIONS

This application claims the benefit of priority to U.S. Provisional Patent Application No. 62/722,521, filed Aug. 24, 2018, which is hereby expressly incorporated by reference in its entirety.

SEQUENCE LISTING

The instant application contains a Sequence Listing which has been submitted electronically in ASCII format and is hereby incorporated by reference in its entirety.

FIELD OF THE INVENTION

Calcium-regulated binding agents are presented. The binding agents are fusion proteins comprising a calcium binding portion and a targeting peptide. The fusion proteins presented herein can be used for in vitro research and for use in diagnosis and treatment. This disclosure is related to Nano-Biomedicine, Nano-Bio-Diagnostic Application (NBDA) and Biomarker Peptides regulated by $Ca^{2+}$.

SUMMARY

In certain aspects, presented herein is a binding agent comprising (a) a calcium binding portion which includes an F-helix peptide and a calcium binding loop peptide derived from an EF-hand motif of a calcium binding protein, wherein the C-terminus of the F-helix peptide is covalently linked to the N-terminus of the calcium binding loop peptide by a peptide bond, and (b) a targeting peptide, wherein the N-terminus of the targeting peptide is covalently linked to the C-terminus of the calcium binding portion by a peptide bond.

In some embodiments, the calcium binding portion comprises a calcium binding portion of an S100 protein, for example a human S100 protein, or another calcium binding protein. In certain embodiments, the calcium binding portion is selected from a sequence listed in Table 4.

In certain embodiments, the F-helix peptide is selected from a peptide sequence listed in Table 3 or a sequence listed in FIG. 2C. In some embodiments, the calcium binding loop peptide is selected from a loop peptide sequence listed in FIG. 2D, or a loop peptide sequence listed in Table 2 or in FIG. 2C.

In some embodiments the targeting peptide comprises one or more peptides selected from a peptide sequence listed in Table 1, a ligand peptide sequence selected from a ligand peptide listed in FIG. 1B or FIG. 1C, or a receptor site sequence selected from a receptor site sequence in Table 1B or Table 1C. In certain embodiments, a targeting peptide comprises 10 to 12 amino acids. In some embodiments, the targeting peptide comprises a portion of an epidermal growth factor receptor (EGFR) that specifically binds to an epidermal growth factor (EGF). In some embodiments, the targeting peptide comprises a portion of a platelet-derived growth factor receptor (PDGFR) that specifically binds to a platelet-derived growth factor (PDGF).

Some aspects include a method of determining the presence of an epidermal growth factor (EGF) or platelet-derived growth factor (PDGF) in a sample comprising: (a) providing a sample obtained from a subject; (b) contacting the sample with a binding agent presented herein; and (c) detecting the presence of a bound complex comprising the binding agent and the EGF, or the binding agent and the PDGF, wherein the presence of the bound complex indicates the presence of an EGF or PDGF in the sample. In some embodiments, the amount of an EGF or PDGF in a sample is determined according an amount of the bound complex detected in the sample. In some embodiments, the binding agent comprises a detectable label. In certain embodiments, the method further comprises contacting the sample with calcium, for example where a final concentration of calcium in the sample is in a range from about 0.01 mM to about 500 mM.

BRIEF DESCRIPTION OF THE DRAWINGS

FIG. 1A.1 and FIG. 1A.2 show the sequence complementarity analysis of different growth factors receptor extracellular domains (bottom portion) and 53 amino acids of EGF with highlighted portions that contribute to receptor binding.

FIG. 1B.1 and FIG. 1B.2 show a statistical calculation of the sequence complementarity for certain 10 amino acid regions derived from EGF for regions of the extracellular loop of various different growth factor receptors.

FIG. 1C.1 and FIG. 1C.2 show a statistical calculation of the sequence complementarity for certain 10 amino acid regions derived from EGF (peptide EGF) for regions of the extracellular loop of various different EGF receptors (CK name). Calcium binding residues are in orange, and residues that form the hydrophobic core of the motif are in green.

DESCRIPTION OF THE INVENTION

Figure 2A:
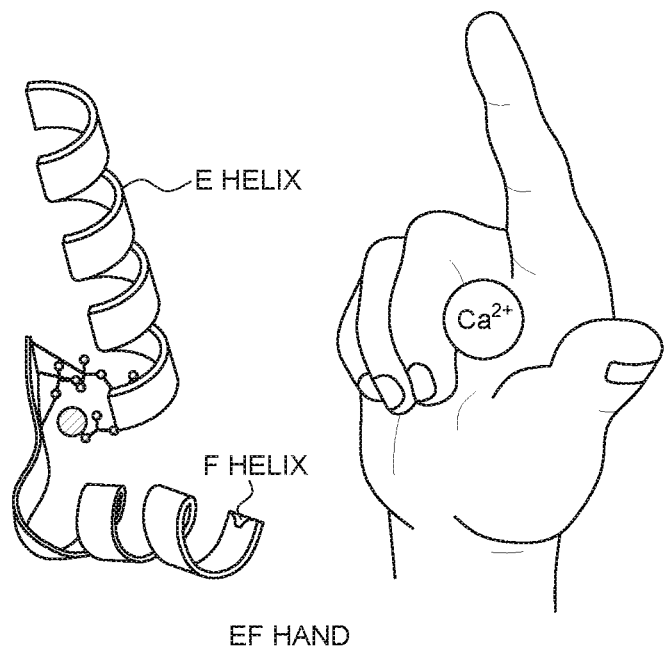
FIG. 2A shows a EF-hand motif comprising an N-terminal F helix domain, a central calcium binding region and a C-terminal E helix.
Figure 2B:
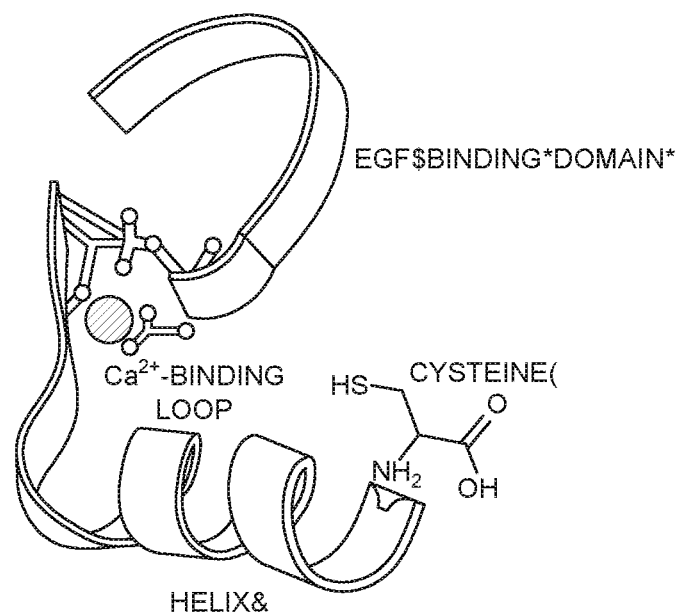
FIG. 2B shows an embodiment of a binding agent where the E-helix of an EF-hand motif is replaced with a targeting peptide comprising receptor binding portion of an EGF.

Multifunctional 'Calcium-Regulated Peptides' (MCRP) is a class of proteins that comprise one or more EF-hand motifs. An EF hand motif is a helix-loop-helix structural domain (e.g., see FIG. 2A). Each EF hand motif comprises a loop region which can bind a $Ca^{2+}$ ion, which binding is coordinated by ligands within the loop region. These peptides typically undergo calcium-dependent conformational changes upon calcium binding that results in revealing a target specific binding-site located in the E helix region.

There are many different EF-hand motifs, which can vary between the different MCRPs, and which differ in calcium affinity.

Presented herein are calcium regulated binding agents comprising a chimeric EF-hand motif. The binding agents can be isolated polypeptides or may be incorporated into other proteins. In some embodiments, a binding agent comprises a calcium binding portion and a targeting peptide. The calcium binding portion of a binding agent often comprises an F-helix peptide and a calcium binding loop peptide derived from an EF-hand motif of a calcium binding protein, wherein the C-terminus of the F-helix peptide is covalently linked to the N-terminus of the calcium binding loop peptide by a peptide bond. The F-helix peptide and calcium binding loop peptide can be derived from the same EF hand motif of a known calcium binding protein, or may be derived from different EF hand motifs of the same or different known calcium binding proteins. Non-limiting examples of known calcium binding proteins that contain EF hand motifs include calbindin proteins, S100 proteins, polcalcin proteins, osteonectin proteins, parvalbumin proteins, calmodulin-like proteins, Eps15 homology domain proteins (EH-domain proteins), Cbp40 proteins (e.g., plasmodial specific call-binding protein LAV1-2), penta-EF hand proteins, and p25-alpha proteins. In some embodiments, the F-helix peptide and a calcium binding loop peptide of a binding agent herein is derived from the EF hand motif of one or more S100 proteins, non-limiting examples of which include S100A1, S100A2, S100A3, S100A4, S100A5, S100A6, S100A7, S100A8, S100A9, S100A10, S100A11, S100A12, S100A13, S100A14, S100A15, S100A16, S100B, S100P and S100Z.

Figure 2C:
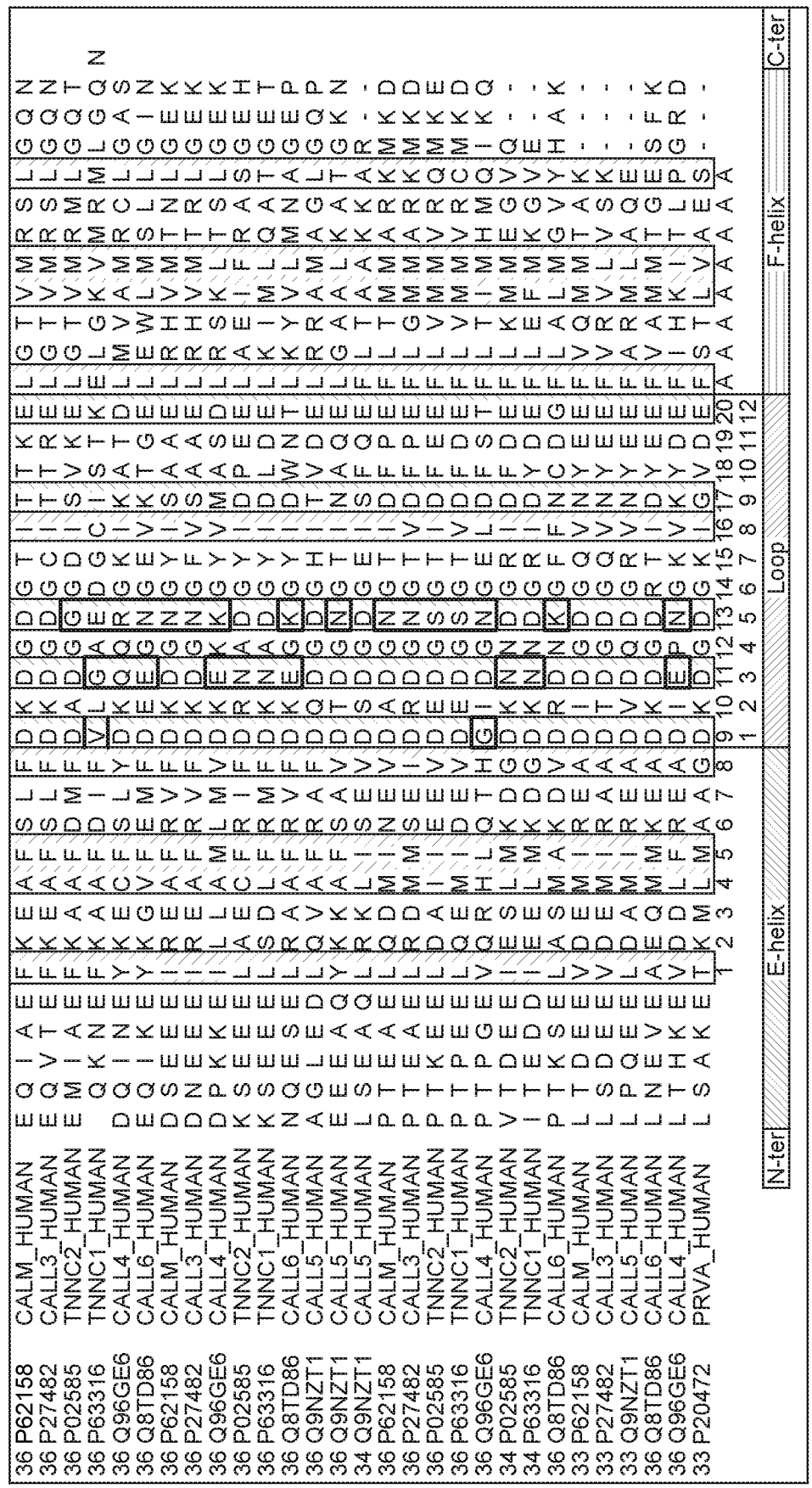
FIG. 2C shows a sequence alignment of the E-helix, loop and F-helix of an EF-hand motif derived from various calcium binding proteins. Uniprot accession numbers of the various calcium binding proteins are provided to the left.
Figure 2D:
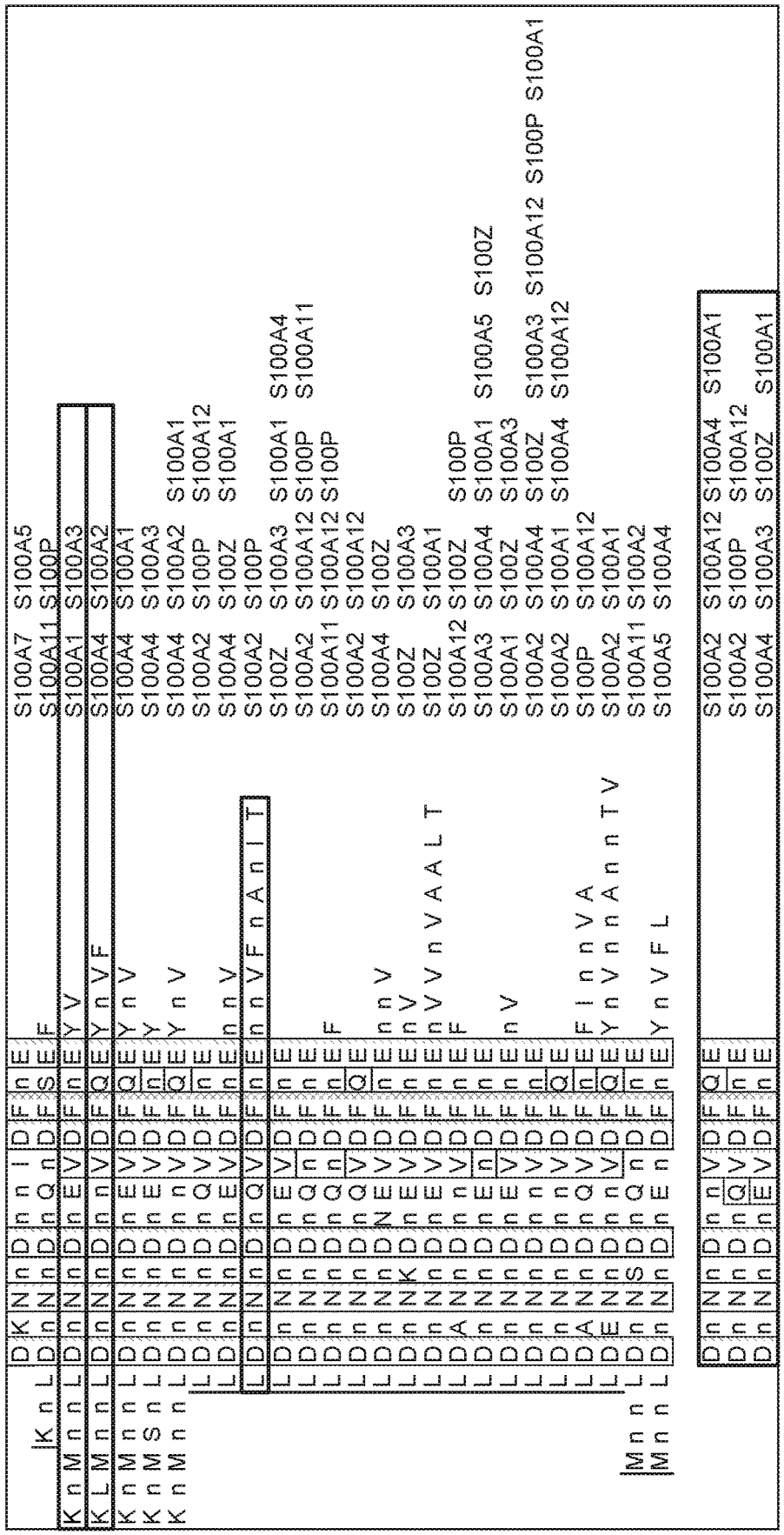
FIG. 2D shows a series of loop peptide sequences of calcium binding loop peptides according to embodiments.

In certain embodiments, the F-helix peptide is selected from a peptide sequence listed in Table 3 or a sequence listed in FIG. 2C. In some embodiments, the calcium binding loop peptide is selected from a loop peptide sequence listed in FIG. 2D, or a loop peptide sequence listed in Table 2 or in FIG. 2C. In certain embodiments, the calcium binding portion is selected from a sequence listed in Table 4.

The calcium binding portion (e.g., F helix peptide and/or calcium binding loop) and/or targeting peptide of a binding agent can be derived, produced, obtained, isolated, and/or purified from any suitable protein and/or any suitable species. Non-limiting examples of a suitable species include mammals (e.g., rabbit, goat, horse, cow, rat, mouse, whale, primate, human), fish, birds (e.g., chickens), insects, bacteria, viruses and plants, for example. In some embodiments a binding agent, or a portion thereof, is derived, produced, obtained, isolated, and/or purified using suitable recombinant methods. In some embodiments a binding agent is produced, obtained, isolated, or purified from a prokaryotic or eukaryotic cell (e.g., a recombinant binding agent produced by a genetically engineered cell). In some embodiments a binding agent is produced, obtained, isolated, or purified from a virus (e.g., a recombinant binding agent produced by a genetically engineered virus). A binding agent can be expressed, isolated from and/or purified from a suitable expression system non-limiting examples of which include a suitable bacteria, phage, insect, virus, plant or mammalian expression system. For example, a nucleic acid encoding a binding agent can be introduced into a suitable mammalian cell line that expresses and secretes the binding agent into the cell culture media.

A binding agent often comprises a targeting peptide. In some embodiments, a targeting peptide is located C-terminal (on the C-terminal side) of the calcium binding portion of an EF-hand motif. In some embodiments, a targeting peptide replaces the E-helix portion of a calcium binding protein. In some embodiments, a targeting peptide replaces a portion of an E-helix of an EF-hand motif of a calcium binding protein. In certain embodiments, a targeting peptide comprises a portion of an E-helix of an EF-hand motif of a calcium binding protein. In some embodiments, a targeting peptide is covalently linked to the C-terminus of the calcium binding portion by a peptide bond. In certain embodiment, a spacer comprising one or more amino acids (e.g., 1 to 20, 1 to 10, 1 to 5, or 1, 2, 3, 4 or 5 amino acids) is placed between the C-terminus of the calcium binding portion and the N-terminus of a targeting peptide to provide a spacer region and/or to provide some flexibility of motion between the targeting peptide and the calcium binding portion. In some embodiments, the amino acid sequence of a spacer is configured to form a helix. In some embodiments a spacer comprises a portion of an E-helix of a calcium binding protein. In some embodiments, a targeting peptide is about 5 to 100, 5 to 50, 5 to 40, 5 to 30, 5 to 25, 5 to 20, 5 to 12, 5 to 11, 5 to 10, 10 to 30, 10 to 20 or 10 to 15 amino acids in length. In some embodiments, a targeting peptide is 9, 10, 11, 12 or 13 amino acids in length.

In certain embodiments, a targeting peptide is configured to bind specifically to a desired biological target. A biological target can be any suitable protein, peptide or a portion thereof. Accordingly, in certain embodiments, a targeting peptide is often a portion of a biological protein that specifically binds specifically to another biological protein (i.e., biological target). In some embodiments, a targeting peptide comprises a single chain antibody, or binding antigen binding portion thereof. In some embodiments, a targeting peptide is a portion of a biological ligand that binds to a biological receptor. In some embodiments, a targeting peptide is a portion of a biological receptor that binds to a biological ligand. Accordingly, a targeting peptide can be derived from any suitable ligand or receptor of a suitable receptor-ligand pair, non-limiting examples of which include an enzyme-substrate, a chemokine receptor-chemokine ligand pair, TNF receptor family member-TNF family member ligand pair (e.g., TNF-TNFR80, TNF-TNFR60, LIGHT-HVEM, OX40-OX40L, CD40-CD154, Fas-FasL, 4-1BB-4-1BB ligand, and the like), a cytokine receptor-ligand pair (e.g., IL2 receptor-IL2, IL4 receptor-IL4, IL4 receptor-IL13, and the like), a toll receptor-ligand pair, a growth factor receptor-ligand pair, antibody-antigen pairs, and the like. Various biological receptor-ligand pairs are known and are published. Bioinformatics methods of identifying binding domains and regions of receptors and ligands that specifically interact are known and are available. Accordingly, a targeting peptide can be derived from any suitable protein or portion thereof that is known to specifically bind to another biological target or protein.

In some embodiments, the targeting peptide comprises a portion of an epidermal growth factor receptor family member protein that specifically binds to an epidermal growth factor (EGF)-family member protein. Alternatively, in some embodiments, the targeting peptide comprises a portion of an epidermal growth factor (EGF)-family member protein that specifically binds to an epidermal growth factor receptor family member protein. An epidermal growth factor receptor family member may be selected from a member of the ErbB family of receptors, non-limiting examples of which include EGFR (ErbB-1), HER2/neu (ErbB-2), Her 3 (ErbB-3) and Her 4 (ErbB-4). An EGF-family member protein may be selected from EGF, Heparin-binding EGF-like growth factor (HB-EGF), transforming growth factor-α (TGF-α), Amphiregulin (AR) Epiregulin (EPR), Epigen, Betacellulin (BTC), neuregulin-1 (NRG1), neuregulin-2 (NRG2) neuregulin-3 (NRG3), and neuregulin-4 (NRG4).

In some embodiments, the targeting peptide comprises a portion of a platelet-derived growth factor (PDGF) receptor family member that specifically binds to a platelet-derived growth factor family member. Alternatively, in some embodiments, the targeting peptide comprises a portion of a platelet-derived growth factor family member protein that specifically binds to a platelet-derived growth factor receptor family member. A platelet-derived growth factor receptor family member may be selected from PDGF-A, PDGF-B, PDGF-C, PDGF-D and homodimers or heterodimers thereof. A platelet-derived growth factor (PDGF) receptor family member may be selected from PDGF receptor-α (PDGFRα), PDGF receptor-β (PDGFRβ) and heterodimers or homodimers thereof.

In some embodiments the targeting peptide comprises one or more peptides selected from a peptide sequence listed in Table 1, a ligand peptide sequence selected from a ligand peptide listed in FIG. 1B or FIG. 1C, or a receptor site sequence selected from a receptor site sequence in Table 1B or Table 1C. In certain embodiments, a targeting peptide comprises 10 to 12 amino acids.

In some aspects presented herein, is a method of determining the presence of an epidermal growth factor (EGF) family member or platelet-derived growth factor (PDGF) family member in a sample comprising (a) providing a sample obtained from a subject, (b) contacting the sample with a binding agent presented herein, and (c) detecting the presence of a bound complex comprising the binding agent and the EGF family member, or a bound complex comprising the binding agent and the PDGF family member, wherein the presence of the bound complex indicates the presence of an EGF or PDGF family member in the sample. In some embodiments, the amount of an EGF or PDGF family member in a sample is determined according an amount of the bound complex detected in the sample.

In some aspects presented herein, is a method of determining the presence of an epidermal growth factor (EGF) receptor family member or platelet-derived growth factor (PDGF) receptor family member in a sample comprising (a) providing a sample obtained from a subject, (b) contacting the sample with a binding agent presented herein, and (c) detecting the presence of a bound complex comprising the binding agent and the EGF receptor family member, or a bound complex comprising the binding agent and the PDGF receptor family member, wherein the presence of the bound complex indicates the presence of the EGF receptor family member or PDGF receptor family member in the sample. In some embodiments, the amount of the EGF receptor family member or PDGF receptor family member in a sample is determined according the amount of the bound complex detected in the sample.

The term "subject" refers to animals, typically mammalian animals. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. In certain embodiments a mammal can be an animal disease model.

In some embodiments a binding agent comprises one or more distinguishable identifiers. Any suitable distinguishable identifier and/or detectable identifier can be used for a composition or method described herein. In certain embodiments a distinguishable identifier can be directly or indirectly associated with (e.g., bound to) a binding agent. For example, a distinguishable identifier can be covalently or non-covalently bound to a binding agent. In some embodiments a distinguishable identifier is bound to or associated with a binding agent and/or a member of binding pair that is covalently or non-covalently bound to a binding agent. In some embodiments a distinguishable identifier is reversibly associated with a binding agent. In certain embodiments a distinguishable identifier is reversibly associated with a binding agent can be removed from a binding agent using a suitable method (e.g., by increasing salt concentration, denaturing, washing, adding a suitable solvent and/or salt, adding a suitable competitor, and/or by heating).

In some embodiments a distinguishable identifier is a label. As used herein, the terms "label" or "labelled" refers to incorporation of a detectable marker. In some embodiments an antibody binding agent comprises a detectable label, non-limiting examples of which include a radiolabel (e.g., an isotope, radioisotopes or radionuclides (e.g., $^{3}$H, $^{14}$C, $^{15}$N, $^{35}$S, $^{90}$Y, $^{99}$TC, $^{125}$I, $^{131}$I), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., horseradish peroxidase, β-galactosidase, luciferase, alkaline phosphatase and the like)), an antibody, an antigen or part thereof, a linker, a member of a binding pair), an enzyme substrate, a small molecule (e.g., biotin, avidin), a mass tag, quantum dots, nanoparticles, the like or combinations thereof. Any suitable fluorophore or light emitting material can be used as a label. A light emitting label can be detected and/or quantitated by a variety of suitable techniques such as, for example, flow cytometry, gel electrophoresis, protein-chip analysis (e.g., any chip methodology), microarray, mass spectrometry, cytofluorimetric analysis, fluorescence microscopy, confocal laser scanning microscopy, laser scanning cytometry, the like and combinations thereof.

In some embodiments a composition or method described herein comprises one or more binding pairs. In certain embodiments one or more members of binding pair comprises a binding agent. In some embodiments a binding pair comprises at least two members (e.g., molecules) that bind non-covalently to (e.g., associate with) each other. Members of a binding pair often bind specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes antibody/antigen, antibody/antibody, antibody/antibody fragment, antibody/antibody receptor, antibody/protein A or protein G, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a binding pair member include an antibody, antibody fragment, reduced antibody, chemically modified antibody, antibody receptor, an antigen, hapten, anti-hapten, a peptide, protein, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. In some embodiments, a member of a binding pair comprises a distinguishable identifier.

In some embodiments a distinguishing identifier, carrier, medication, toxic compound and/or a suitable polypeptide can be indirectly or directly associated with, or bound to (e.g., covalently bound to, or conjugated to), a binding agent. In certain embodiments agents or molecules are sometimes conjugated to or bound to binding agents to alter or extend the in vivo half-life of a binding agent. In some embodiments, a binding agent is fused or associated with one or more polypeptides (e.g., a toxin, ligand, receptor, cytokine, antibody, the like or combinations thereof). In certain embodiments, a binding agent is linked to a half-life extending vehicle known in the art. Such vehicles include, but are not limited to, polyethylene glycol, glycogen (e.g., glycosylation of the antigen binding protein), and dextran. Such vehicles are described, e.g., in U.S. application Ser. No. 09/428,082, now U.S. Pat. No. 6,660,843 and published PCT Application No. WO 99/25044, the disclosures of which are hereby incorporated by reference in their entirety.

In some embodiments, toxin, peptide, carrier, distinguishable identifier, or a member of a binding pair is bound to a binding agent by a linker. A linker can provide a mechanism for covalently attaching a toxin, peptide, carrier, distinguishable identifier, or a member of a binding pair to a binding agent. Any suitable linker can be used in a composition or method described herein. Non-limiting examples of suitable linkers include silanes, thiols, phosphonic acid, and polyethylene glycol (PEG). Methods of attaching two or more molecules using a linker are well known in the art and are sometimes referred to as "crosslinking". Non-limiting examples of crosslinking include an amine reacting with a N-Hydroxysuccinimide (NETS) ester, an imidoester, a pentafluorophenyl (PFP) ester, a hydroxymethyl phosphine, an oxirane or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

A portion of a binding agent (e.g., a calcium binding portion, an F-helix peptide, a calcium binding loop or a targeting peptide) may comprise or consist of a peptide that is at least 80%, at least 85%, at least 90%, at least 95% or 100% identical to corresponding peptide of another protein. The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences.

In certain embodiments, a method disclosed herein comprises contacting a sample with a binding agent and an amount of calcium. In some embodiments, a sample is contacted with an amount of calcium to provide a final concentration of calcium in the sample in a range from about 0.001 mM to about 1000 mM, about 0.01 mM to about 500 mM, about 0.1 mM to about 300 mM or about 1 mM to about 200 mM. In some embodiments, a binding agent described herein binds to a suitable target defined by the binding specificity of the targeting peptide portion of the binding agent. As described herein, in some embodiments, the targeting peptide portion of a binding agent binds to a target protein only in the presence of calcium.

TABLE 1

| Sequence Identifier | Target Peptide | Targeting Protein |
|---|---|---|
| SEQ ID NO: 1 | EALDKYACNC | EGFR |
| SEQ ID NO: 2 | DGYCLHDGVC | PGFRA\PGFRB |
| SEQ ID NO: 3 | MYIELALDKYA | EGFR\PGFRB |
| SEQ ID NO: 4 | CNCVVGYIGE | PGFRA\ERBB2\PGFRB |
| SEQ ID NO: 5 | RCQYRDLKWW | EGFR |
| SEQ ID NO: 6 | YRDLKWWELR | EGFR |
| SEQ ID NO: 7 | VVGYIGERCQ | EGFR\ERBB2\PGFRB |
| SEQ ID NO: 8 | CLHDGVCMYI | PGFRA |
| SEQ ID NO: 9 | SECPLSHDGY | ERBB2\PGFRB |
| SEQ ID NO: 10 | NSDSECPLSH | PGFRA\ERBB2\PGFRB |

TABLE 2

| Sequence Identifier | Calcium Binding Loop Peptide |
|---|---|
| SEQ ID NO: 11 | DKDGDGTITTKE |
| SEQ ID NO: 12 | DKDGDGCITTRE |
| SEQ ID NO: 13 | DADGGGDISVKE |
| SEQ ID NO: 14 | VLGAEDGCISTK |
| SEQ ID NO: 15 | DKQQRGKIKATD |
| SEQ ID NO: 16 | DEEGNGEVKTGE |

TABLE 2-continued

| Sequence Identifier | Calcium Binding Loop Peptide |
|---|---|
| SEQ ID NO: 17 | DKDGNGYISAAE |
| SEQ ID NO: 18 | DKDGNGFVSAAE |
| SEQ ID NO: 19 | DKEKKGYVMASD |
| SEQ ID NO: 20 | DRNADGYIDPEE |
| SEQ ID NO: 21 | DKNADGYIDLDE |
| SEQ ID NO: 22 | DKEGKGYIDWNT |
| SEQ ID NO: 23 | DQDGDGHITVDE |
| SEQ ID NO: 24 | DTDGNGTINAQE |
| SEQ ID NO: 25 | DSDGDGEISFQE |
| SEQ ID NO: 26 | DADGNGTIDFPE |
| SEQ ID NO: 27 | DRDGNGTVDFPE |
| SEQ ID NO: 28 | DEDGSGTIDFEE |
| SEQ ID NO: 29 | DEDGSGTVDFDE |
| SEQ ID NO: 30 | GIDGNGELDFST |
| SEQ ID NO: 31 | DKNNDGRIDFDE |
| SEQ ID NO: 32 | DKNNDGRIDYDE |
| SEQ ID NO: 33 | DRDNKGFFNCDG |
| SEQ ID NO: 34 | DIDGDGQVNYEE |
| SEQ ID NO: 35 | DTDGDGQVNYEE |
| SEQ ID NO: 36 | DVDQDGRVNYEE |
| SEQ ID NO: 37 | DKDGDRTIDYEE |
| SEQ ID NO: 38 | DIEPNGKVKYDE |
| SEQ ID NO: 39 | DKDGDGKIGVDE |

TABLE 3

| Sequence Identifier | F-Helix Peptide |
|---|---|
| SEQ ID NO: 40 | LGTVMRSLGQN |
| SEQ ID NO: 41 | LGTVMRMLGQT |
| SEQ ID NO: 42 | ELGKVMRMLGQN |
| SEQ ID NO: 43 | LMVAMRCLGAS |
| SEQ ID NO: 44 | LEWLMSLLGIN |
| SEQ ID NO: 45 | LRHVMTNLGEK |
| SEQ ID NO: 46 | LRHVMTRLGEK |
| SEQ ID NO: 47 | LRSKLTSLGEK |
| SEQ ID NO: 48 | LAEIFRASGEH |
| SEQ ID NO: 49 | LKIMLQATGET |
| SEQ ID NO: 50 | LKYVLMNAGEP |

TABLE 3-continued

| Sequence Identifier | F-Helix Peptide |
|---|---|
| SEQ ID NO: 51 | LRRAMAGLGQP |
| SEQ ID NO: 52 | LGAALKATGKN |
| SEQ ID NO: 53 | FLTAAKKAR |
| SEQ ID NO: 54 | FLTMMARKMKD |
| SEQ ID NO: 55 | FLGMMARKMKD |
| SEQ ID NO: 56 | FLVMMVRQMKE |
| SEQ ID NO: 57 | FLVMMVRCMKD |
| SEQ ID NO: 58 | FLTIMHMQIKQ |
| SEQ ID NO: 59 | FLKMMEGVQ |
| SEQ ID NO: 60 | FLEFMKGVE |
| SEQ ID NO: 61 | FLALMGVYHEK |
| SEQ ID NO: 62 | FVQMMTAK |
| SEQ ID NO: 63 | FVRVLSK |
| SEQ ID NO: 64 | FARMLAQE |
| SEQ ID NO: 65 | FVAMMTGESFK |
| SEQ ID NO: 66 | FIHKITLPGRD |
| SEQ ID NO: 67 | FSTLVAES |

TABLE 4

| Sequence Identifier | Calcium Binding Portion |
|---|---|
| SEQ ID NO: 68 | DKDGDGTITTKELGTVMRSLGQN |
| SEQ ID NO: 69 | DKDGDGCITTRELGTVMRSLGQN |
| SEQ ID NO: 70 | DADGGGDISVKELGTVMRMLGQT |
| SEQ ID NO: 71 | VLGAEDGCISTKELGKVMRMLGQN |
| SEQ ID NO: 72 | DKQQRGKIKATDLMVAMRCLGAS |
| SEQ ID NO: 73 | DEEGNGEVKTGELEWLMSLLGIN |
| SEQ ID NO: 74 | DKDGNGYISAAELRHVMTNLGEK |
| SEQ ID NO: 75 | DKDGNGFVSAAELRHVMTRLGEK |
| SEQ ID NO: 76 | DKEKKGYVMASDLRSKLTSLGEK |
| SEQ ID NO: 77 | DRNADGYIDPEELAEIFRASGEH |
| SEQ ID NO: 78 | DKNADGYIDLDELKIMLQATGET |
| SEQ ID NO: 79 | DKEGKGYIDWNTLKYVLMNAGEP |
| SEQ ID NO: 80 | DQDGDGHITVDELRRAMAGLGQP |
| SEQ ID NO: 81 | DTDGNGTINAQELGAALKATGKN |
| SEQ ID NO: 82 | DSDGDGEISFQEFLTAAKKAR |
| SEQ ID NO: 83 | DADGNGTIDFPEFLTMMARKMKD |
| SEQ ID NO: 84 | DRDGNGTVDFPEFLGMMARKMKD |
| SEQ ID NO: 85 | DEDGSGTIDFEEFLVMMVRQMKE |

TABLE 4-continued

| Sequence Identifier | Calcium Binding Portion |
|---|---|
| SEQ ID NO: 86 | DEDGSGTVDFDEFLVMMVRCMKD |
| SEQ ID NO: 87 | GIDGNGELDFSTFLTIMHMQIKQ |
| SEQ ID NO: 88 | DKNNDGRIDFDEFLKMMEGVQ |
| SEQ ID NO: 89 | DKNNDGRIDYDEFLEFMKGVE |
| SEQ ID NO: 90 | DRDNKGFFNCDGFLALMGVYHEK |
| SEQ ID NO: 91 | DIDGDGQVNYEEFVQMMTAK |
| SEQ ID NO: 92 | DTDGDGQVNYEEFVRVLSK |
| SEQ ID NO: 93 | DVDQDGRVNYEEFARMLAQE |
| SEQ ID NO: 94 | DKDGDRTIDYEEFVAMMTGESFK |
| SEQ ID NO: 95 | DIEPNGKVKYDEFIHKITLPGRD |
| SEQ ID NO: 96 | DKDGDGKIGVDEFSTLVAES |

EXAMPLES

Example 1

A binding agent is designed in silico configured to have a calcium-dependent binding interaction with Epidermal Growth Factor (EGF) which interaction is defined by targeting peptide region located at the C-terminal end of the binding agent. This specific binding agent comprises an F-helix peptide joined to a loop region specific for calcium binding, and a targeting peptide region of 9 amino acids in length at the C-terminus derived from the Epidermal Growth Factor Receptor (EGFR) which recognizing and binds to EGF (e.g., see Ref 1). EGF is a 53 amino acids peptide that promotes proliferation of the cells of the epidermis. EGF is a growth factor that plays an important role in the regulation of cell growth, proliferation, and differentiation by binding to its receptor EGFR. Human EGF is a 6045-Da protein with 53 amino acid residues and three intramolecular disulfide bonds (Ref. 2).

The calcium binding portion of the binding agent comprises the calcium binding loop and F-helix of an S100 protein. In this particular example, the binding agent comprises the calcium binding loop and F-helix of human-S100A2.

S100 proteins are named because they are soluble at 100% ammonium sulphate solution. S100 proteins constitute one of the largest families of EF-hand proteins which includes at least 21 different low-molecular weight S100 proteins, each displaying unique properties (Ref. 3-4). Typical S100 proteins are characterized by two calcium-binding sites. S100 proteins are small, acidic proteins containing a classical $Ca^{2+}$-binding EF-hand at the C-terminus and a S100-specific EF-hand at the N-terminus (Ref. 5-9). Most S100 proteins show a cell- and tissue-specific expression indicating specialized biological functions. S100 proteins form homodimers and heterodimers and even oligomers, which contribute to their functional diversification. S100 proteins act intracellularly as $Ca^{2+}$-signaling molecules, but some members are secreted from cells and act in a cytokine-like manner through the receptor for advanced glycation end products (RAGE) or other receptors (Ref. 10).

S100 proteins are involved in a variety of cellular processes like cell cycle regulation, cell growth, cell differentiation and motility. Interestingly, of the 20 human genes, 16 are tightly clustered in region 1q21 of human chromosome. Target binding found in the second loop (C-terminal region) of an S100 protein (i.e., a region of about 10 to 12 residues) is typically $Ca^{2+}$-dependent. A set of CRPs profiles, targeting different proteins can be used to facilitate diagnosis and/or prognosis information on treatment options and monitor patient response to treatments (Ref 11-12).

REFERENCES

1. Carl Branden and John Tooze, illustrated book Introduction to Protein Structure, New York: Garland Publishing Company, 302 Pages, 1991).
2. Carlpenter and Cohen, 1990; Schlessinger et al. 1983. The presence of at least two sub-classes of EGF binding sites in EGF-responsive cells.
3. Marenholz, I., Heizmann, C. W., & Fritz, G. 2004; Biochem. Biophys. Res. Commun 322, 1111-1122.
4. Marenholz, I., Lovering, R. C., & Heizmann, C. W. 2006; Biochem. Biophys. Acta Mol. Cell Res., 1763, 1282-1283
5. Fritz, G., & Heizmann, C. W. 2004; Handbook of Matalloproteins (A. Messerchmidt, W. Bode, & M. Cygler, eds.), Vol. 3, John Wiley & Sons, pp. 529-540.
6. Bhattacharya, S., Bunick, C. G., & Chazin, W. J. 2004; Biochem. Biophys. Acta 1742, 69-79.
7. Vallely, K. M., Rustandi, R. R., Ellis, K. C., Varlamova, O., Bresnick, A. R., & Weber, D. J. 2002; Biochemistry 41, 12670-12680.
8. Ikura, M., & Ames, J. B. 2006; Proc. Natl. Acad. Sci. USA 103, 1159-1164.
9. Zimmer, D. B., Chaplin, J., Baldwin, A., & Rast, M. 2005; Cell Mol. Biol. (Noisy-le-grand) 51, 201-214.
10. Ramasamy, R., Vannucci, S. J., Yan, S. S., Herold, K., Yan, S. F., & Schmidt, A. M. 2005; Glycobiology 15, 16R-28R.
11. Joachim Krebs, & Claus W. Heizmann. 2007; Calcium-binding proteins and the EF-hand principle., Elsevier B. V., Chapter 3, 51-93.
12. Hongyan Chen, Chengshan Xu, Qing'e Jin, Zhihua Liu. 2014; Am J Cancer Res 4(2): 89-115

What is claimed is:

1. A binding agent comprising:
   (a) a calcium binding portion; and
   (b) a targeting peptide, wherein the N-terminus of the targeting peptide is covalently linked to the C-terminus of the calcium binding portion by a peptide bond;
   wherein the calcium binding portion is selected from the group consisting of one or more of SEQ ID NOS. 68-96, and
   wherein the targeting peptide is selected from the group consisting of one or more of SEQ ID NOS. 1-10.

2. A method of determining the presence of an epidermal growth factor receptor (EGFR) family member in a sample, said method comprising:
   (a) providing a sample obtained from a subject,
   (b) contacting the sample with the binding agent of claim 1, the binding agent comprising a targeting peptide selected from SEQ ID Nos. 1, 3, 5, 6, and 7 that binds to an epidermal growth factor receptor family member protein, and
   (c) detecting the presence of a bound complex comprising the binding agent and the EGFR family member wherein the presence of the bound complex indicates the presence of the EGFR family member in the sample.

3. The method of claim 2, wherein the amount of the EGFR family member in the sample is determined according to an amount of the bound complex detected in (c).

4. A method of determining the presence of a platelet derived growth factor receptor (PDGFR) family member in a sample, said method comprising:
   (a) providing a sample obtained from a subject,
   (b) contacting the sample with the binding agent of claim 1, the binding agent comprising a targeting peptide selected from SEQ ID Nos. 2-4, and 7-10 that binds to a platelet derived growth factor receptor family member protein, and
   (c) detecting the presence of a bound complex comprising the binding agent and the PDGFR family member wherein the presence of the bound complex indicates the presence of the PDGFR family member in the sample.

5. The method of claim 4, wherein the amount of the PDGFR family member in the sample is determined according to an amount of the bound complex detected in (c).

6. The method of claim 2, further comprising contacting the sample with calcium prior to (c), wherein a final concentration of calcium in the sample is within the range from about 0.01 mM to about 500 mM.

7. The method of claim 4, further comprising contacting the sample with calcium prior to (c), wherein a final concentration of calcium in the sample is within the range from about 0.01 mM to about 500 mM.

* * * * *